US009265626B1

(12) United States Patent
Lecomte et al.

(10) Patent No.: US 9,265,626 B1
(45) Date of Patent: Feb. 23, 2016

(54) HEIGHT-ADJUSTABLE THREADED SHOCK ABSORBING MODULE AND ASSOCIATED COUPLING MEMBER

(75) Inventors: Christophe Lecomte, Reykjavik (IS); Vilhjalmur Freyr Jónsson, Reykjavik (IS)

(73) Assignee: Össur hf, Reykjavik (IS)

( * ) Notice: Subject to any disclaimer, the term of this patent is extended or adjusted under 35 U.S.C. 154(b) by 216 days.

(21) Appl. No.: 13/149,118

(22) Filed: May 31, 2011

(51) Int. Cl.
*A61F 2/68* (2006.01)
*A61F 2/66* (2006.01)
*A61F 2/30* (2006.01)

(52) U.S. Cl.
CPC ..... *A61F 2/6607* (2013.01); *A61F 2002/30329* (2013.01)

(58) Field of Classification Search
CPC .................................................... A61F 2/6607
USPC ...................................................... 623/52, 56
See application file for complete search history.

(56) References Cited

U.S. PATENT DOCUMENTS

| | | | | |
|---|---|---|---|---|
| 5,181,932 A | * | 1/1993 | Phillips | 623/52 |
| 5,181,933 A | * | 1/1993 | Phillips | 623/55 |
| 5,458,656 A | | 10/1995 | Phillips | |
| 5,486,209 A | * | 1/1996 | Phillips | 623/52 |
| 5,514,186 A | * | 5/1996 | Phillips | 623/52 |
| 5,593,457 A | * | 1/1997 | Phillips | 623/52 |
| 6,302,918 B1 | | 10/2001 | Gramnas | |
| 6,478,826 B1 | * | 11/2002 | Phillips et al. | 623/27 |
| 6,511,512 B2 | | 1/2003 | Phillips et al. | |
| 6,602,295 B1 | | 8/2003 | Doddroe et al. | |
| 6,863,695 B2 | | 3/2005 | Doddroe et al. | |
| 6,887,279 B2 | | 5/2005 | Phillips et al. | |
| 7,169,190 B2 | | 1/2007 | Phillips et al. | |
| 8,025,699 B2 | * | 9/2011 | Lecomte et al. | 623/52 |

(Continued)

OTHER PUBLICATIONS

Endolite elite blade VT product brochure, http://www.endolite.co.uk/products/feet/eliteblade/eliteblade_foot.html, available before May 31, 2011.

(Continued)

*Primary Examiner* — Jacqueline Woznicki
(74) *Attorney, Agent, or Firm* — Knobbe, Martens, Olson & Bear, LLP.

(57) ABSTRACT

Systems and apparatuses are provided comprising a prosthetic foot, a shock absorbing module and a coupling member for operably connecting the prosthetic foot to the shock absorbing module. The prosthetic foot can include an upper member connected to a lower member, wherein the upper member includes an upper attachment portion for attaching to the coupling member. The coupling member can include one or more holes for receiving an epoxy filling to secure the coupling member to the upper attachment portion of the prosthetic foot. The shock absorbing member can include a threaded portion that is mateable with an inner threaded section of the coupling member, thereby allowing height adjustability of the shock absorbing member.

17 Claims, 8 Drawing Sheets

(56) References Cited

U.S. PATENT DOCUMENTS

| | | | |
|---|---|---|---|
| 2002/0082712 A1* | 6/2002 | Townsend et al. | 623/52 |
| 2002/0143408 A1* | 10/2002 | Townsend et al. | 623/55 |
| 2002/0147500 A1* | 10/2002 | Wilkinson et al. | 623/35 |
| 2003/0220701 A1* | 11/2003 | Steinbarger et al. | 623/38 |
| 2005/0038525 A1 | 2/2005 | Doddroe et al. | |
| 2005/0071017 A1* | 3/2005 | Lecomte et al. | 623/52 |
| 2005/0267603 A1* | 12/2005 | Lecomte et al. | 623/52 |
| 2006/0004467 A1* | 1/2006 | Lecomte et al. | 623/35 |
| 2006/0224246 A1* | 10/2006 | Clausen et al. | 623/24 |
| 2009/0287315 A1* | 11/2009 | Lecomte et al. | 623/55 |
| 2010/0174219 A1* | 7/2010 | Franke et al. | 602/16 |

OTHER PUBLICATIONS

Össur Ceterus product; Ossur Prosthetics Product Catalog, pp. 204-212, 2005.

Össur Re-Flex Rotate product, catalog pages available at http://www.ossur.com/?PageID=15418, announced on website Nov. 2010.

Össur Re-Flex VSP product, Ossur Prosthetics Product Catalog, pp. 187-194, 2005.

* cited by examiner

HEIGHT-ADJUSTABLE THREADED SHOCK ABSORBING MODULE AND ASSOCIATED COUPLING MEMBER

BACKGROUND

1. Field

The present application relates to foot prostheses in general, and more particularly, to a prosthetic foot connected to a shock absorbing module and a coupling mechanism for connecting the prosthetic foot to the shock absorbing module.

2. Description of the Related Art

Various types of prosthetic foot devices are available as substitutes for human feet. The prosthetic foot devices can be coupled to shock absorbing modules comprising one or more pylons that connect the prosthetic foot to an upper stump. The pylons provide a strong and sturdy extension structure between the stump and the prosthetic foot.

While various coupling mechanisms are available to secure the prosthetic foot to the shock absorbing modules, they often suffer from deficiencies. For example, coupling mechanisms that rely on bolts passing through the prosthetic foot and into the shock absorbing modules can reduce strength of both of the members. In addition, bolts can be heavy, resulting in less comfort for the user of a prosthetic foot. And, often times, conventional coupling mechanisms cannot accommodate height adjustments of the shock absorbing module.

SUMMARY

Certain embodiments of the present application include a prosthetic system. In one embodiment, the prosthetic system comprises a prosthetic foot; a height-adjustable shock absorbing module; and a coupling member. The prosthetic foot comprises an upper member secured to a lower member, and the upper member includes an upper attachment portion and a split that separates the upper member into a lateral blade and a medial blade. The height-adjustable shock absorbing module comprises a torque-resistant cuff member, an inner pylon, an outer pylon, an inner resilient element, and an external threaded portion extending along a length of the outer pylon. The coupling member comprises a rear section and a front section. The rear section includes a recess for receiving the upper attachment portion of the prosthetic foot and one or more inlet holes for receiving a curable material to secure the coupling member to the prosthetic foot; the front section includes a receiving portion having inner threads for receiving the threaded portion of the shock absorbing module and a clamping mechanism having at least one screw hole for receiving at least one screw for tightening the receiving portion in preparation for securing the threaded portion of the shock absorbing module to the coupling member.

In another embodiment, a prosthetic system comprises a prosthetic foot comprising an upper member secured to a lower member; a shock absorbing module comprising at least one pylon; and a coupling member configured to couple to the prosthetic foot and the shock absorbing module, wherein the coupling member includes a recess for receiving a portion of the prosthetic foot and one or more inlet holes for receiving a curable material for securing the coupling member to the prosthetic foot.

In another embodiment, a prosthetic system comprises a prosthetic foot comprising an upper member secured to a lower member; a shock absorbing module comprising at least one pylon and an external threaded portion that extends along a length of the pylon; and a coupling member configured to couple to the prosthetic foot and the shock absorbing module, wherein the coupling member includes a receiving portion having inner threads for receiving and mating with the threaded portion of the shock absorbing module.

In yet another embodiment, a prosthetic system comprises a prosthetic foot comprising a generally vertically extending rear portion; a shock absorbing module comprising at least one pylon; and a coupling member configured to couple the prosthetic foot and the shock absorbing module, wherein the coupling member is configured to receive at least a portion of the generally vertically extending rear portion of the prosthetic foot and the pylon of the shock absorbing module.

For purposes of summarizing the disclosure, certain aspects, advantages and novel features have been described herein. It is to be understood that not necessarily all such advantages may be achieved in accordance with any particular embodiment. Thus, the disclosure may be embodied or carried out in a manner that achieves or optimizes one advantage or group of advantages as taught herein without necessarily achieving other advantages as may be taught or suggested herein.

DETAILED DESCRIPTION OF THE EMBODIMENTS

Figure 1A:
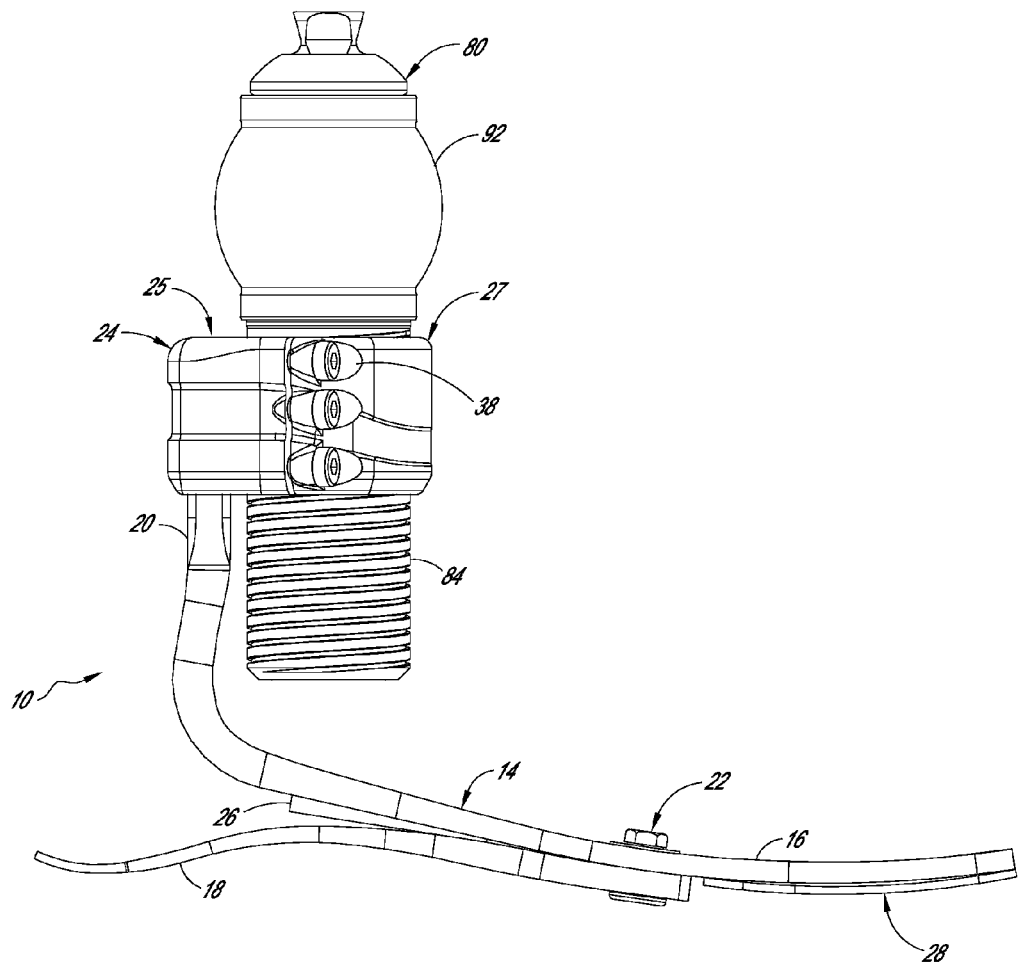
FIG. 1A illustrates a side view of a prosthetic foot coupled to a height-adjustable threaded shock module according to embodiments of the present application.

The present application is directed to a prosthetic foot 10 coupled to a height-adjustable threaded shock absorbing module. The prosthetic foot is coupled to the shock absorbing module using a novel coupling member that is configured to receive a hardenable material, such as a curable material, to secure the prosthetic foot to the shock absorbing module. By using a curable material to secure the coupling member to the prosthetic foot, this removes the need to use bolts through the prosthetic foot components, thereby maintaining the strength of the components for more long-term use.

FIGS. 1A-1E illustrate various views (side, rear, top perspective, top and side cross-sectional, respectively) of a prosthetic foot coupled to a height-adjustable threaded shock module according to embodiments of the present application. As shown in the illustrated embodiment, a prosthetic foot 14 includes an upper member 16 in contact with a lower member 18. The upper member 16 of the prosthetic foot 14 includes an upper attachment portion 20. A coupling member 24 is provided that secures the upper attachment portion 20 of the prosthetic foot to a height-adjustable threaded shock module 80.

In some embodiments, the prosthetic foot 14 can include an upper plate-like member 16 in direct contact with a lower plate-like member 18. As shown in FIG. 1A, the upper member 16 is curvilinear, and includes an upper attachment portion 20 that extends downward and forward to an anterior portion comprising a toe portion. A bottom surface of the upper member 16 is attached to a top surface of the lower member 18. The lower member 18 can include an arch portion that extends to a posterior portion comprising a heel portion. In some embodiments, the arch portion can receive an insole member, such as an insole member of a foot cover or cosmesis that fits over the prosthetic foot. Example insoles and foot covers are described in U.S. Publication No. 2010/0004757, filed Mar. 24, 2009, titled "Smooth Rollover Insole for Prosthetic Foot" and U.S. Publication No. 2006/0015192, filed May 26, 2005, titled "Functional Foot Cover," respectively, the disclosures of which are both hereby incorporated by reference in their entirety and should be considered a part of this specification. The upper member 16 and lower member 18 can be attached using one or more adhesives or fasteners (e.g., screws 22). In other embodiments, the prosthetic foot 14 can comprise a single foot plate. The foot plate can have a generally horizontal portion that contacts the ground and a generally vertical portion that engages with the coupling member 24. Alternatively, the foot plate can have an overall curved shape.

FIGS. 1A-1D show an embodiment of the prosthetic foot 14 comprising at least one resilient member, e.g., wedge 26, optionally insertable in a slot between the upper member 16 and lower member 18. In the illustrated embodiment, the slot is located in a rear portion of the prosthetic foot 10. The wedge 26 is configured to alter the stiffness characteristics of the lower member and influence the fluidity of the heel to toe loading of the prosthetic foot 10 during ambulation. The at least one wedge 26 is preferably removably disposed in the slot between the upper member 16 and the lower member 18. Optionally, a plurality of wedges 26 can be disposed in the slot. In another embodiment, the at least one wedge 26 can be fixed in the slot via, for example, an adhesive. Various other mechanisms can be used to fix the wedge 26 in the slot. For example, the wedge 26 can be bolted or screwed, adhered, or clamped to the lower member 18 and/or the upper member 16. The at least one wedge 26 is preferably configured to provide additional shock absorption to the prosthetic foot 14. In one embodiment, the wedge 26 can be made, for example, of a hard plastic, such as polyurethane or polypropylene. The wedge 26 can also be made of a more compressible material, such as foam, natural or synthetic rubbers, or the like. However, the wedge 26 can be made of any material configured to provide adequate shock absorption to the prosthetic foot 14. A set of such wedges 26 can also be provided, wherein each wedge 26 has a different stiffness. In some embodiments, the wedge 26 can be between about 40 and 60 mm long, between about 30 and 55 mm wide, and between about 2 and 16 mm tall, though the wedge 26 can have other suitable dimensions. The wedge 26 can also have a durometer of between about 60 A and 95 A in some embodiments. In another embodiment, the wedge 26 has a durometer of about 85 A. Further details on resilient members, among other things, can be found in U.S. application Ser. No. 10/642,125, filed Aug. 15, 2003, the entire contents of which are incorporated herein by reference and should be considered a part of this specification.

With continued reference to the embodiment illustrated in FIGS. 1A-1D, a crepe portion 28 can be attached to the underside of the anterior portion of the upper member 16 and aligned with the anterior portion of the upper member 16 so as to not extend past the anterior portion. In another embodiment (not shown), the crepe portion 28 can extend forwardly of the anterior edge of the upper member 16. The crepe portion 28 can be a resilient pad or cushion made of a compressible material. In one embodiment, the crepe portion 28 can also be made of a porous material. In another embodiment, the crepe portion 28 can be made of solid urethane. In one embodiment, the crepe portion 28 is attached to the anterior portion of the upper member 16 with an adhesive. However, other attachment mechanisms can be used, such as bolts, screws, clamps and bands wrapped around the crepe portion 28 and the upper member 16. The crepe portion 28 can have a shape corresponding to the shape of the upper member 16. For example, the crepe portion 28 can have a rounded edge corresponding to the rounded edge of the front end. In the illustrated embodiment, the crepe portion 28 has a uniform thickness. In another embodiment, the crepe portion 28 can have a varying thickness. For example, the crepe portion 28 can have a decreasing thickness in the direction of the front end of the upper member 16. In other embodiments, the upper member 16 does not have a crepe portion 28 attached to it, so that the anterior portion of the upper member 16 operatively contacts the support surface. Further details on the crepe portion can be found in U.S. application Ser. No. 10/642,125, which is incorporated by reference in its entirety above.

Figure 1B:
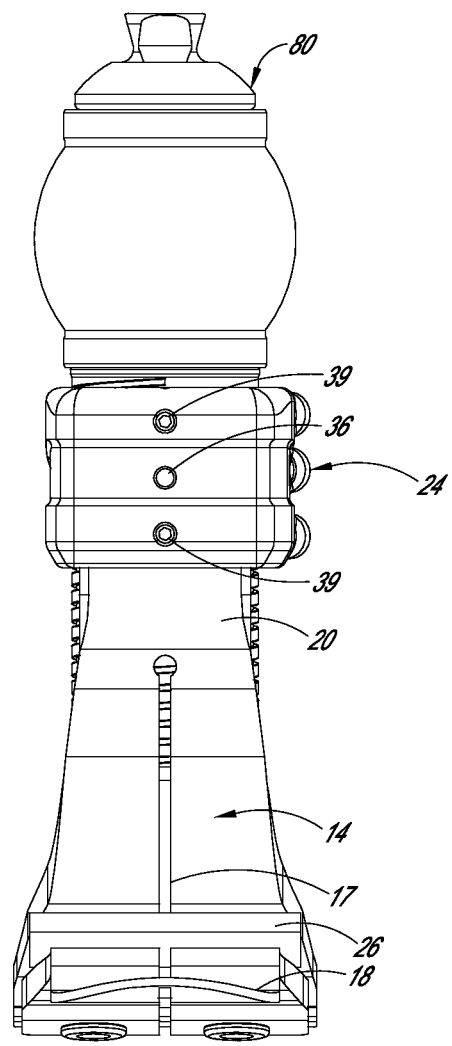
FIG. 1B illustrates a rear view of the prosthetic foot coupled to a height-adjustable threaded shock module of FIG. 1A.
Figure 1C:
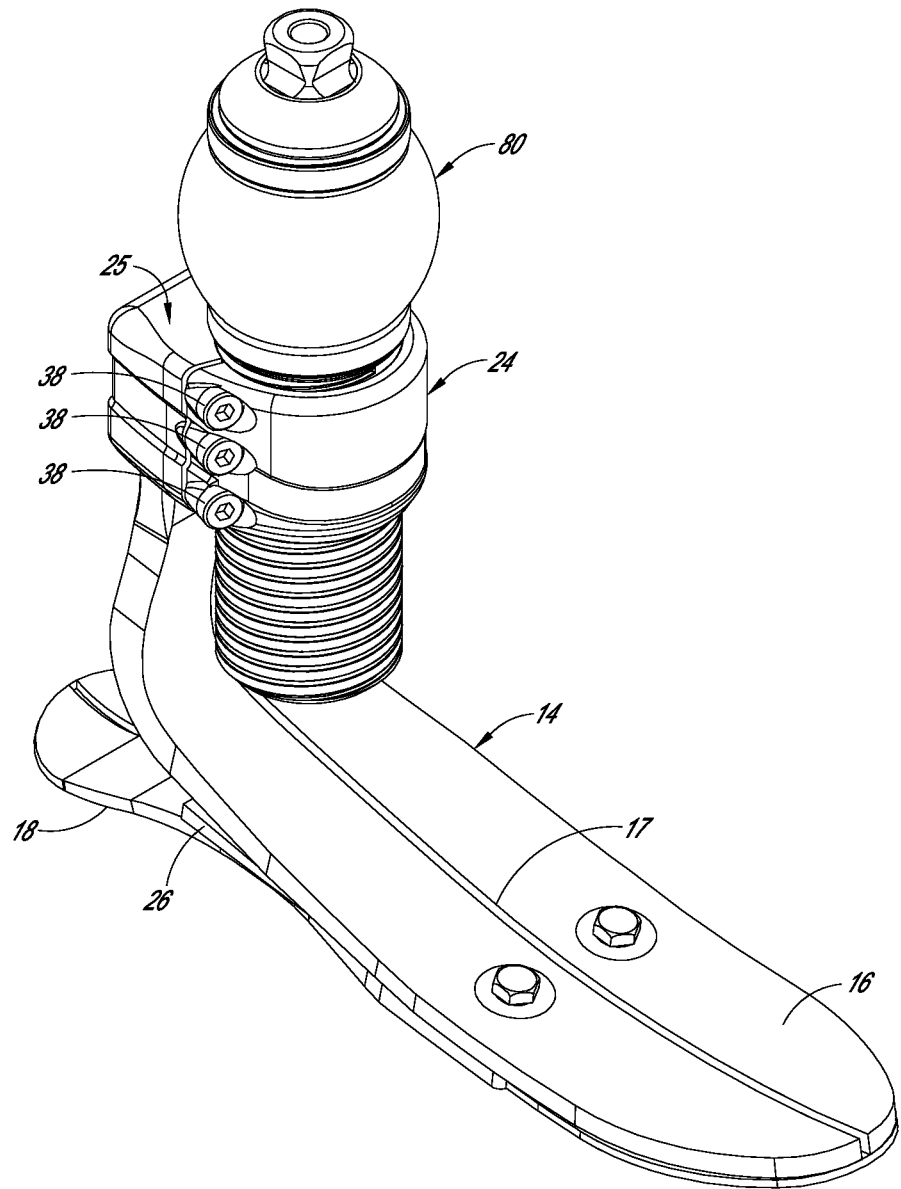
FIG. 1C illustrates a top perspective view of the prosthetic foot coupled to a height-adjustable threaded shock module of FIG. 1A.
Figure 1D:
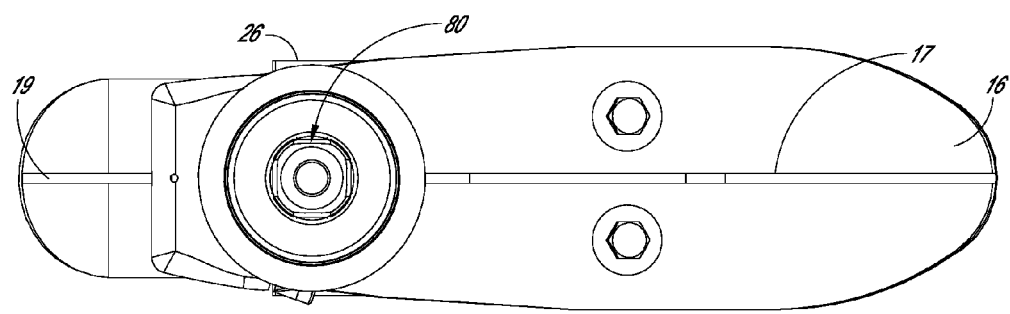
FIG. 1D illustrates a top view of the prosthetic foot coupled to a height-adjustable threaded shock module of FIG. 1A.
Figure 1E:
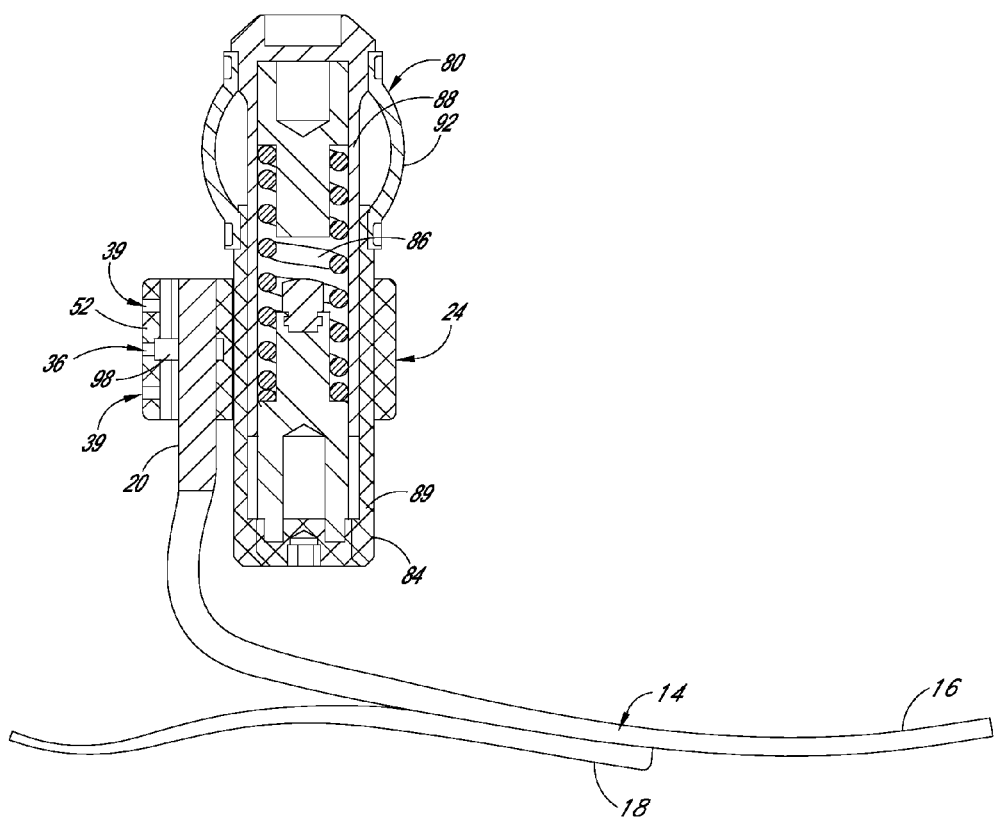
FIG. 1E illustrates a partial cross-sectional side view of some of the components of the prosthetic foot and height-adjustable threaded shock module of FIG. 1A.

As shown in FIGS. 1B-1E, the upper member 16 of the prosthetic foot can include a split 17. The split 17 can extend from an anterior edge of the prosthetic foot (shown in FIG. 1C) to a rear portion of the prosthetic foot. While the split 17 is illustrated as extending to a point slightly below the upper attachment portion 20 of the prosthetic foot, in some embodiments, the split 17 extends through the upper attachment portion 20. The split 17 can be positioned substantially midway along a longitudinal axis such that it splits the prosthetic foot into medial and lateral blades of approximately similar width. In other embodiments, the split 17 is slightly off-set from the longitudinal axis such that the medial and lateral blades are not of similar width. Moreover, while the split 17 is illustrated as substantially straight, in other embodiments, the split can curve in one or more directions (e.g., curve medially or laterally). Examples of a prosthetic foot having a curving slit are described in U.S. Publication No. 2009/0287315, filed Jul. 24, 2009, titled "Foot Prosthesis with Resilient Multi-Axial Ankle," the disclosure of which is hereby incorporated by reference in its entirety. In still other embodiments, the split 17 can extend partially along the length of the prosthetic foot. In some embodiments, the lower member 18 can also include a split 19 that at least partially separates the lower member 18 into medial and lateral blades as shown in FIG. 1D. Additionally, in some embodiments, the crepe portion 28 can also include a longitudinal split that is configured to align with the split 17 in the upper member 16. The splits 17 and 19 are provided to advantageously assist in providing multi-axial movement capabilities similar to those of a natural human foot and increased stability of the prosthetic foot during ambulation (e.g., over uneven terrain).

In some embodiments, the upper member 16 and/or lower member 18 can be formed of lightweight, strong materials, such as graphite, fiberglass, carbon fiber or the like. In some embodiments, the upper member 16 and/or lower member 18 can be formed of multiple layers of material.

The shock absorbing module 80 can comprise an inner pylon 88 and an outer pylon 89 having an external threaded portion 84, as well as an internal resilient element 86 (shown in FIG. 1E) in the form of a coil compressible spring that can provide impact absorption during operation of the prosthetic foot 14. In other embodiments, the internal resilient element can comprise a compressible fluid. In some cases, the shock module comprises an internal resilient element 86 (e.g., spring) in combination with a compressible fluid such as air. The internal resilient element 86 in the form of a spring can be fixed with respect to the inner pylon 88. A torque-resistant cuff member 92 provides torsion-resistance to the prosthesis and also keeps dirt and other debris from getting between pylons 88 and 89.

As shown in FIG. 1A, the shock absorbing module includes an outer pylon 89 with an external threaded portion 84. The thread portion 84 extends along a length of the outer pylon 89, from approximately the base of the cuff-member 92 to a bottom section of the outer pylon 89. The external threaded portion 84 cooperates with internal threads of the coupling member 24, thereby advantageously allowing for the shock absorbing module 80 to be adjusted in an upward and downward direction. In some embodiments, rotation of the threaded portion 84 in a clockwise direction moves the shock absorbing module 80 in one axial direction (e.g., downward), while rotation of the threaded portion 84 in a counter-clockwise direction move the shock absorbing module 80 in an opposite axial direction (e.g., upward). In other embodiments, counter-clockwise rotation can result in an upward direction, while clockwise rotation of the threads can result in a downward direction. The shock absorbing module 80 can thus change its relative height, and thus serves as a height-adjustable threaded shock module. By moving the shock module 80 in an upward direction, the cuff member 92 is moved further away vertically from the coupling member 24 and the ground. In contrast, by moving the shock module 80 in a downward direction, the cuff member 92 is moved closer vertically to the coupling member 24 and the ground.

The prosthetic foot 14 and the shock absorbing module 80 can be operably connected by a coupling member 24. As shown in FIG. 1A, the upper attachment portion 20 of the prosthetic foot 14 is received upwardly into a rear section 25 of the coupling member 24, while the threaded portion of the shock-absorbing pylon module 80 is received downwardly into a front section 27 of the coupling member 24.

The coupling member 24 is configured such that it receives a curable material in a rear recess 50 (shown in FIG. 2E) via one or more inlet holes 36 formed in the rear section 25. The curable material can be, for example, a thermosetting plastic, such as epoxy. Various types of epoxy fillings can be used, including low sag epoxy filling. Anchors or barbs can be used to hold the components in place to allow for the use of other thermoplastic materials. The curable material helps to bind and secure the prosthetic foot 14 (e.g., via its upper attachment portion 20) to an inner surface of the coupling member 24. Advantageously, the curable material replaces the need to drill holes into the upper attachment portion 20 of the prosthetic foot and/or the pylons of the shock absorbing module 80 in order to receive securing bolts. As drilling holes for bolting in the prosthetic foot 14 and/or shock absorbing module 80 may lower the strength of each member, the use of a curable material advantageously helps to preserve the strength of each member for more long-term use. In addition, the use of bolts and washers, which are generally composed of stainless materials, can be quite heavy, such that the use of lighter-weight curable material is more comfortable to the user. Further, epoxy fillings have good fatigue properties and would not pre-stress the prosthetic foot 14 and/or shock-absorbing pylon module 80 like bolts when a torque is applied.

In addition to the one or more inlet holes 36 for receiving a curable material, the coupling member 24 can also include one or more holes 39 for receiving set screws or fasteners. The holes 36, 39 can extend through a rear wall 52 of the coupling member 24 so as to be in communication with the recess 50. As shown in FIG. 1B, in some embodiments, the prosthetic foot includes a single inlet hole 36 for receiving a curable material, and two adjacent holes 39 for receiving set screws. The set screws (not shown) can be used prior to or during the injection of the curable material into the inlet hole 36 to push against the surface of the upper attachment member 20 of the prosthetic foot 14, so as to generally fix the upper attachment member 20 relative to the coupling member 24. The upper attachment member 20 is thereby advantageously secured in between the set screws and an inner surface of the rear section 25 of the coupling member 24 while the settable material is hardening (e.g., while the curable material is curing). In other words, the set screws help to hold the upper attachment member 20 together with the coupling member 24 until the curable material is fully cured. In some embodiments, after the curable material is fully cured, the set screws remain in place, while in other embodiments it is possible to remove the set screws from the holes 39 after the curable material has cured.

The coupling member 24 is also configured such that it includes a clamping mechanism 54 in a front section 27. The clamping mechanism 54 is configured to receive one or more screws that can help tighten and secure the coupling member 24 (e.g., via the pylon receiving portion 29 shown in FIG. 2C) to the threaded portion 84 of the shock absorbing module 80. Prior to securing the coupling member 24 to the shock absorbing module 80 via the clamping mechanism 54, the user can advantageously adjust the height of the shock absorbing module 80 in an upward or downward motion in order to maximize comfort to the user. Unlike the present application, conventional coupling members that rely on bolts through the shock absorbing module (e.g., via its pylons) do not provide height adjustability. More details of the coupling member 24 are provided with respect to FIGS. 2A-2E.

FIGS. 2A-2E illustrate various views (side, rear, top perspective, top and an alternative bottom perspective, respectively) of a coupling member according to embodiments of the present application. Additional advantageous features of the coupling member 24 are shown in these figures and discussed below.

Figure 2A:
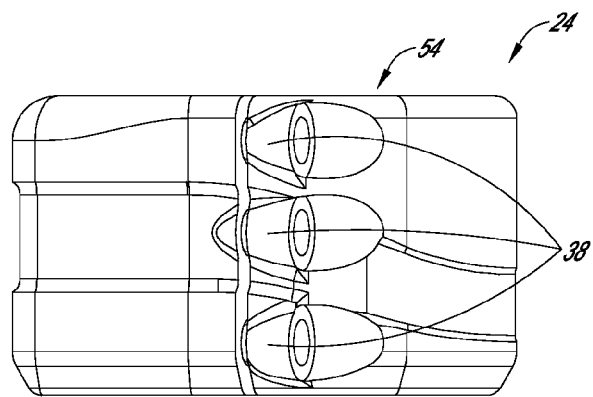
FIG. 2A illustrates a side view of a coupling member according to embodiments of the present application.

FIG. 2A illustrates a side view of a coupling member 24 configured to couple the upper attachment portion 20 of the prosthetic foot 14 to the shock absorbing module 80. From this view, a plurality of screw holes 38 are illustrated for receiving a plurality of screws (not shown) for tightening the receiving portion 29 in preparation for securing the threaded portion of the shock absorbing module 80 to the coupling member. As shown in FIG. 2D, prior to inserting the screws 40 into the screw holes 38, the front section 27 of the coupling member 24 includes a gap 71. Once one or more of the screws (not shown) are screwed in place in the coupling member 24, the gap 71 is narrowed and/or closed partially or completely, thereby providing a tightened ring formation for receiving the threaded portion 84 of the shock module 80.

Figure 2B:
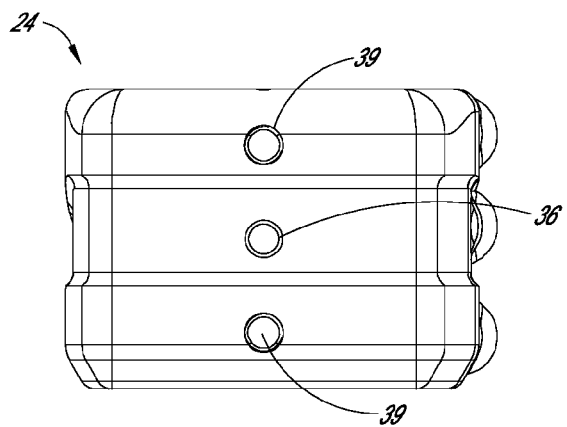
FIG. 2B illustrates a rear view of the coupling member of FIG. 2A.

FIG. 2B illustrates a rear view of the coupling member 24. From this view, the hole 36 for receiving the curable material and the holes 39 for receiving the set screws are visible. While the holes 36 and 39 appear to be of similar size and shape, in some embodiments, the holes are of different size and/or shape.

Figure 2C:
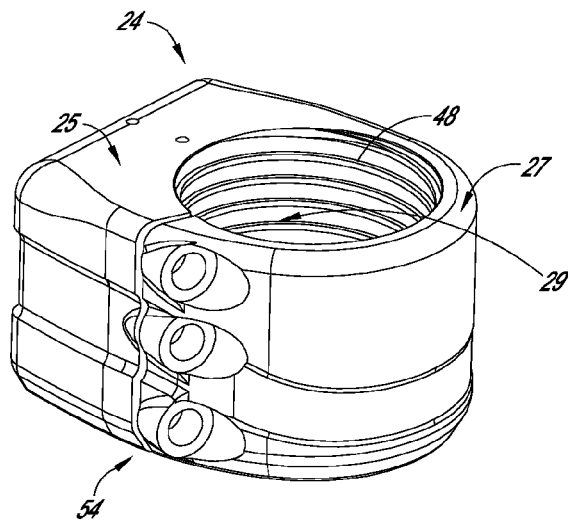
FIG. 2C illustrates a top perspective view of the coupling member of FIG. 2A.
Figure 2D:
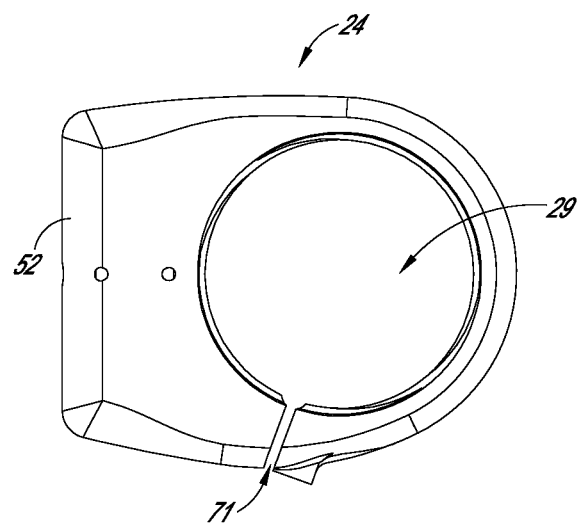
FIG. 2D illustrates a top view of the coupling member of FIG. 2A.

FIG. 2C illustrates a top perspective view of the coupling member 24. From this view, the receiving portion 29 for receiving the threaded portion 84 of the shock absorbing module 80 is visible. The receiving portion 29 is encompassed by a plurality of inner threads 48 formed on the inner surface of the receiving portion 29. The inner threads 48 of the coupling member 24 are configured to advantageously mate with the threads of the threaded portion 84. For example, in some embodiments, once the coupling member 24 is ready to receive a shock absorbing module 80 (e.g., after screws 40 have been screwed into the screw holes 38 to narrow the gap 71 shown in FIG. 2D), the threaded portion 84 of the pylon can be rotated either clockwise or counterclockwise to mate with the matching inner threads 48 of the threaded portion 84.

As shown in FIG. 2C, the top portion of the rear section 25 of the coupling member 24 can be completely or substantially covered. In contrast, the bottom of the rear section 25 of the coupling member 24 opens to form a recess 50 (shown in FIG. 2E) for receiving the upper attachment portion 20 of the prosthetic foot. In another embodiment, the recess 50 can extend through the coupling member 24 from top to bottom so as to define an opening through the rear section 25 of the coupling member 24.

FIG. 2D illustrates a top view of the coupling member 24. From this view, the receiving portion 29 and the associated gap 71 of the receiving portion 29 are visible. In some embodiments, once screws (not shown) are inserted through screw holes 38, the gap 71 is narrowed and/or closed partially or completely.

Figure 2E:
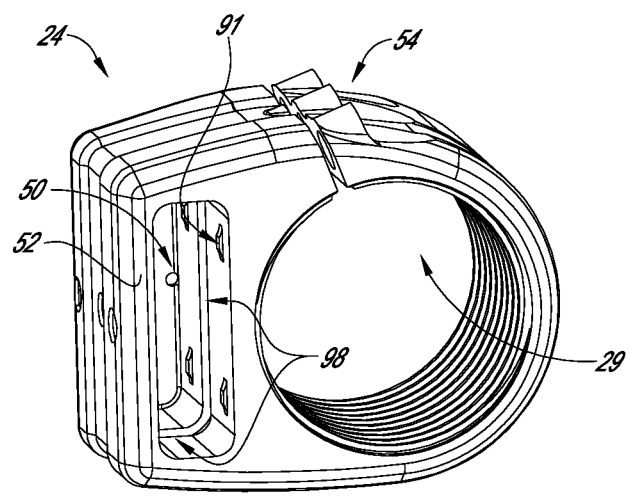
FIG. 2E illustrates a bottom perspective view of the coupling member of FIG. 2A.

FIG. 2E illustrates a bottom view of the coupling member 24. From this view, the recess 50 in the rear section 25 of the coupling member 24 and the receiving portion 29 of the front section 27 are visible. The recess 50 in the rear section 25 is sized and configured to receive an upper attachment portion 20 of the prosthetic foot. The recess 50 includes protrusions 91 for supporting the upper attachment portion 20 and ensuring the correct gap for the curable material to flow. The upper attachment portion 20 of the prosthetic foot is pushed against the protrusions 91 using the set screws. The protrusions therefore advantageously allow for proper alignment of the upper attachment portion 20 of the prosthetic foot and the coupling member 24, while allowing the curable or settable material to flow around the protrusions. From this view, the inner threads 48 of the receiving portion 29 for mating with the threaded portion 84 of the shock absorbing module are also visible.

Figure 3:
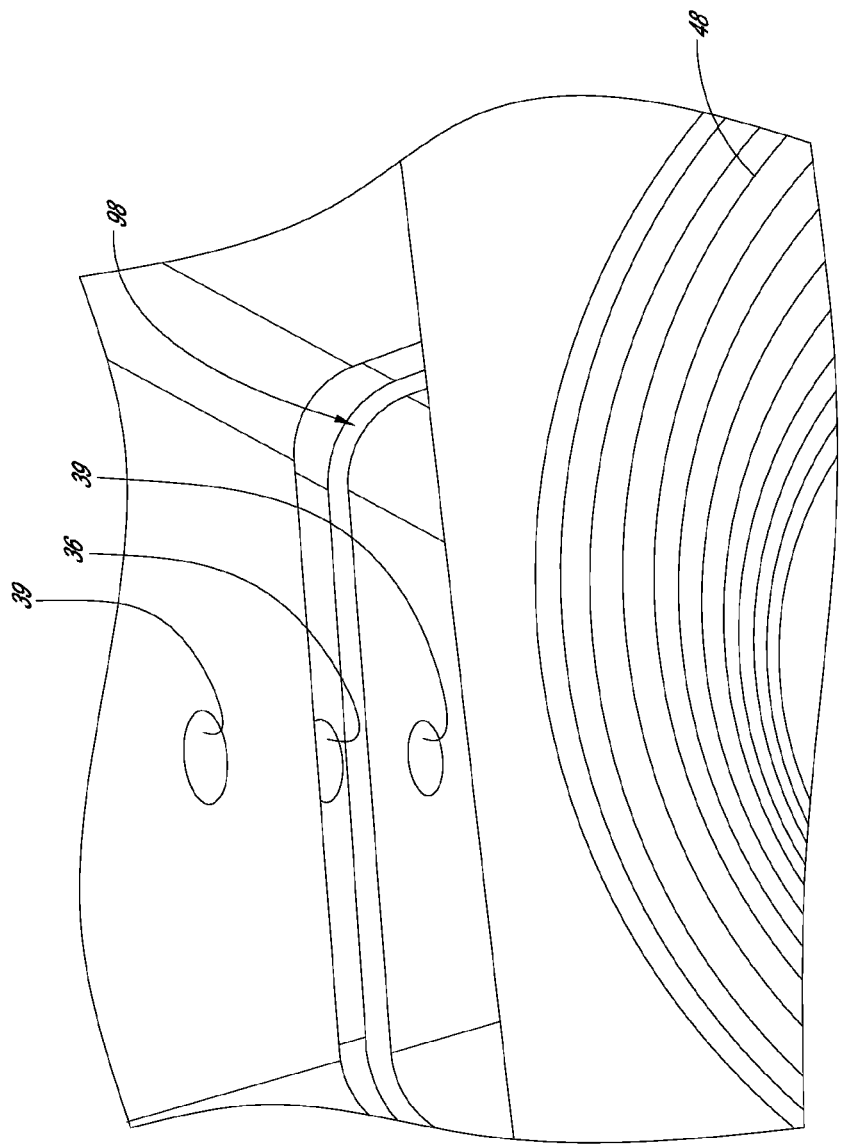
FIG. 3 illustrates an enlarged sectional view of a portion of the coupling member according to embodiments of the present application.

FIG. 3 illustrates an exploded view of an inner portion of the coupling member including a channel for guiding curable material according to embodiments of the present application. From this perspective, a hole 36 for receiving a curable material and a hole for receiving a set screw 39 are visible. Also shown is a channel 98 that extends around the inner perimeter of the recess 50 or opening in the rear section 25 of the coupling member 24. The channel 98 advantageously allows for the curable material to flow around all sides of the recess 50 or opening in the rear section 25 coupling member 24, thereby ensuring that the curable material flows on all sides of the upper attachment portion 20 to generally surround the upper attachment portion 20.

Of course, the foregoing description is that of certain features, aspects and advantages of the present invention, to which various changes and modifications can be made without departing from the spirit and scope of the present invention. Moreover, the prosthetic foot need not feature all of the objects, advantages, features and aspects discussed above. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. For example, features described or illustrated in connection with one disclosed embodiment can also be used in connection with a second disclosed embodiment, even if the features are not illustrated in drawings for the second embodiment. Accordingly, it should be understood that various features and aspects of the disclosed embodiments can be combined with or substituted for one another in order to form varying modes of the discussed prosthetic foot. Thus, it is intended that the present invention cover the modifications and variations of this invention provided that they come within the scope of the appended claims or their equivalents.

What is claimed is:

1. A prosthetic system comprising:
   a prosthetic foot comprising an upper member secured to a lower member;
   a shock absorbing module comprising at least one pylon and an external threaded portion that extends along a length of the pylon; and
   a coupling member configured to couple to the prosthetic foot and the shock absorbing module, wherein the coupling member includes a recess for receiving at least a portion of the prosthetic foot and a receiving portion having inner threads for receiving and mating with the threaded portion of the shock absorbing module, wherein the recess is completely separate from the receiving portion, wherein the recess completely encircles the portion of the prosthetic foot and a central axis extending through the receiving portion along which the receiving portion receives the shock absorbing module is parallel and horizontally spaced apart from a central axis extending through the recess along which the recess receives the portion of the prosthetic foot when the prosthetic foot is at rest on a support surface, and wherein the shock absorbing module is configured to rotate relative to the coupling member to adjust a height of the shock absorbing module.

2. The prosthetic system of claim 1, wherein the upper member includes a curved split that separates the upper member into a medial blade and a lateral blade.

3. The prosthetic system of claim 1, wherein the lower member includes a curved split that separates the lower member into a medial blade and a lateral blade.

4. The prosthetic system of claim 1, wherein the shock absorbing module comprises an internal resilient element comprising a spring member.

5. The prosthetic system of claim 4, wherein the internal resilient element further comprises a compressible fluid.

6. The prosthetic system of claim 1, further comprising a settable material for securing the prosthetic foot to the coupling member, wherein the recess is configured to receive the settable material through an inlet hole in fluid communication with the recess.

7. The prosthetic system of claim 6, wherein the recess further comprises a channel for receiving the settable material, and the channel is aligned and in fluid communication with the inlet hole.

8. The prosthetic system of claim 1, wherein the coupling member includes a clamping mechanism including one or more holes for receiving one or more screws.

9. The prosthetic system of claim 1, wherein the coupling member includes a rear portion including at least one hole for receiving a curable material and at least one hole for receiving a set screw.

10. A prosthetic system comprising:
   a prosthetic foot comprising an upper member secured to a lower member, the upper member including a split that separates the upper member into a lateral blade and a medial blade and an upper attachment portion, wherein the upper attachment portion extends vertically, and wherein the upper member extends downward and curves rearwardly from the upper attachment portion and then extends downwardly and curves forwardly and extends to a generally planar distal toe portion;
   a height-adjustable shock absorbing module comprising a torque-resistant cuff member, an inner pylon, an outer pylon, an inner resilient element, and an external threaded portion extending along a length of the outer pylon; and
   a coupling member comprising a rear section and a front section, the rear section including a recess for receiving at least a portion of the upper attachment portion of the prosthetic foot and one or more inlet holes for receiving an epoxy filling to secure the coupling member to the prosthetic foot, the front section including a receiving portion having inner threads for receiving the threaded portion of the shock absorbing module and a clamping mechanism having at least one screw hole for receiving at least one screw for tightening the receiving portion to secure the threaded portion of the shock absorbing module to the coupling member, wherein the recess is completely separate from the receiving portion, wherein the front section is configured to be entirely anterior to the upper attachment portion of the prosthetic foot when the foot is at rest on a support surface and the upper attachment portion of the foot extends generally vertically, wherein the shock absorbing module is configured to rotate relative to the coupling member to adjust a height of the shock absorbing module, and wherein a lower end of the shock absorbing module is configured to extend below a lowermost end of the coupling member such that the lower end of the shock absorbing module is disposed in front of and laterally spaced apart from the upper attachment portion of the prosthetic foot and such that at a lowest position of the shock absorbing module wherein the cuff is adjacent an upper side of the coupling member, a length of the shock absorbing module disposed below the lowermost end of the coupling member is at least as great as a height of the coupling member.

11. The prosthetic system of claim 1, wherein the receiving portion extends about a first vertical axis and the recess extends about a second vertical axis, the first vertical axis parallel to the second vertical axis.

12. A prosthetic system comprising:
   a prosthetic foot comprising a generally vertically extending rear portion;
   a shock absorbing module comprising a torque-resistance cuff and at least one pylon; and
   a coupling member configured to couple the prosthetic foot and the shock absorbing module, wherein the coupling member comprises a recess defined between and bounded by a rear wall, a front wall, an open bottom end, and a closed top end at a top of the coupling member and configured to receive at least a portion of the generally vertically extending rear portion of the prosthetic foot and the coupling member comprises a receiving portion configured to receive the pylon of the shock absorbing module, the receiving portion being completely separate from the recess and the coupling member configured such that the shock absorbing module is spaced apart from the generally vertically extending rear portion of the prosthetic foot in a direction perpendicular to a longitudinal central axis of the shock absorbing module, wherein the shock absorbing module is configured to rotate relative to the coupling member to adjust a height of the shock absorbing module, and wherein a lower end of the shock absorbing module is configured to extend below a lowermost end of the coupling member such that at a lowest position of the shock absorbing module wherein the cuff is adjacent an upper side of the coupling member, a length of the shock absorbing module disposed below the lowermost end of the coupling member is at least as great as a height of the coupling member.

13. The prosthetic system of claim 12, wherein the recess is in a rear section of the coupling member.

14. The prosthetic system of claim 13, wherein the coupling member includes one or more inlet holes in fluid communication with the recess for receiving a settable material for securing the generally vertically extending rear portion prosthetic foot to the coupling member.

15. The prosthetic system of claim 14, wherein the recess of the coupling member further comprises one or more channels in fluid communication with the one or more inlet holes for receiving the settable material, wherein the one or more channels extend around an inner perimeter of the recess so that the one or more channels extend and direct the settable material circumferentially about the portion of the prosthetic foot when inserted into the recess of the coupling member.

16. The prosthetic system of claim 12, wherein the coupling member includes a receiving portion in a front section having inner threads for receiving and mating with an external threaded portion of the pylon of the shock absorbing module.

17. The prosthetic system of claim 16, wherein the front section of the coupling member further comprises a clamping mechanism configured to tighten the receiving portion and secure the coupling member to the pylon of the shock absorbing module.

* * * * *